(12) United States Patent  
Jones et al.

(10) Patent No.: US 9,060,599 B1  
(45) Date of Patent: Jun. 23, 2015

(54) FOLDING BEDSIDE TABLE

(71) Applicants: Brenda Verbois Jones, Denham Springs, LA (US); Kevin Mark Jones, Tomball, TX (US)

(72) Inventors: Brenda Verbois Jones, Denham Springs, LA (US); Kevin Mark Jones, Tomball, TX (US)

( * ) Notice: Subject to any disclaimer, the term of this patent is extended or adjusted under 35 U.S.C. 154(b) by 0 days.

(21) Appl. No.: 14/155,673

(22) Filed: Jan. 15, 2014

(51) Int. Cl.
A47B 23/02 (2006.01)
A47B 23/06 (2006.01)
A47B 23/00 (2006.01)

(52) U.S. Cl.
CPC ............... *A47B 23/06* (2013.01); *A47B 23/00* (2013.01)

(58) Field of Classification Search
CPC .................................... A47C 21/00; A61G 7/05
USPC ............. 5/507.1, 503.1, 658, 659, 662; 108/42–44, 49
See application file for complete search history.

(56) References Cited

U.S. PATENT DOCUMENTS

| | | | | |
|---|---|---|---|---|
| 2,733,455 A * | 2/1956 | Stuart et al. | | 5/507.1 |
| 3,009,676 A * | 11/1961 | Buchwald | | 248/229.11 |
| 3,174,162 A * | 3/1965 | Sinton | | 5/503.1 |
| 3,435,469 A * | 4/1969 | Fricke | | 5/504.1 |
| 4,537,452 A * | 8/1985 | Rice et al. | | 312/314 |
| 5,509,158 A * | 4/1996 | Morrison | | 5/504.1 |
| 5,699,565 A * | 12/1997 | Petterborg | | 5/504.1 |
| 6,591,762 B1 * | 7/2003 | Haghayegh | | 108/42 |
| 7,360,260 B2 * | 4/2008 | Gallawa et al. | | 5/2.1 |
| D652,931 S | 1/2012 | Petteway | | |
| D652,932 S | 1/2012 | Petteway | | |
| 8,397,647 B1 * | 3/2013 | Riegel | | 108/24 |
| 2008/0083351 A1 * | 4/2008 | Lippert et al. | | 108/44 |
| 2011/0126353 A1 * | 6/2011 | Veenendaal | | 5/428 |

OTHER PUBLICATIONS

Jeffrey Mark Petteway, http://www.cpapholders.com/product/features.

* cited by examiner

*Primary Examiner* — Timothy D Collins
*Assistant Examiner* — Richard G Davis
(74) *Attorney, Agent, or Firm* — Kevin M. Jones; Alex Deese

(57) ABSTRACT

Described herein is a support for a Constant Positive Airway Pressure (CPAP) machine. The support comprises a table for supporting the CPAP with portion extended between the mattresses of the bed, and a stabilizer extending downward from the bottom of the table surface to brace against the lower mattress. The table may be foldable for travel purposes. The table also comprises a hook for securing the power cord, and a raised lip around the edge of the table top to prevent accidentally knocking the device from the table surface. A hook extending from one side of the table top provided a convenient place to store a CPAP mask between uses.

3 Claims, 5 Drawing Sheets

FOLDING BEDSIDE TABLE

CROSS-REFERENCE TO RELATED APPLICATIONS

Not Applicable

STATEMENT REGARDING FEDERALLY SPONSORED RESEARCH OR DEVELOPMENT

Not Applicable

REFERENCE TO SEQUENCE LISTING, A TABLE, OR A COMPUTER PROGRAM LISTING COMPACT DISC APPENDIX

Not Applicable

BACKGROUND OF THE INVENTION

People who utilize Constant Positive Airway Pressure (CPAP) machines when they sleep often have dedicated locations for those machines on their bedside table or favorite napping chair. But when traveling, a problem often arises. Bedside tables may be nonexistent, or may be crowded with standard essentials such as alarm clocks, lamps, phones, remotes, etc. When a guest in someone's home, one may be hesitant to rearrange a decorative table top to accommodate a CPAP machine for the night. Hotel rooms often use smaller furniture to make rooms look larger, again not allowing room for a CPAP to be placed near the bed without extensive rearranging of the surface's contents.

One option is to place the machine in the top drawer of a bedside table, which works provided the drawer is not full of other items, and is large enough to accommodate the CPAP without blocking air intakes located on a lower edges of the machines. However, doing so may cause the opened drawer to fall during the night.

Another option is to place the machine on the bed. However, the machines are easily knocked off the bed during restless sleep, stretching hoses to the point of disconnecting them, or worst breaking. Noise from the falling machine can awaken others, and the fall may break the machine, or at least damage the delicate calibrations of the machine's working components.

Another option is to place the machine on the floor by the bed. If the bed is sufficiently raised, this does not allow sufficient hose for the user's unrestricted sleep. Further, the air intakes are drawing air from floor level, possibly under the bed where settled dust and dirt more quickly clogs filters, and/or is generally less healthy to breath throughout the night.

DETAILED DESCRIPTION OF THE PREFERRED EMBODIMENTS

Figure 1A:
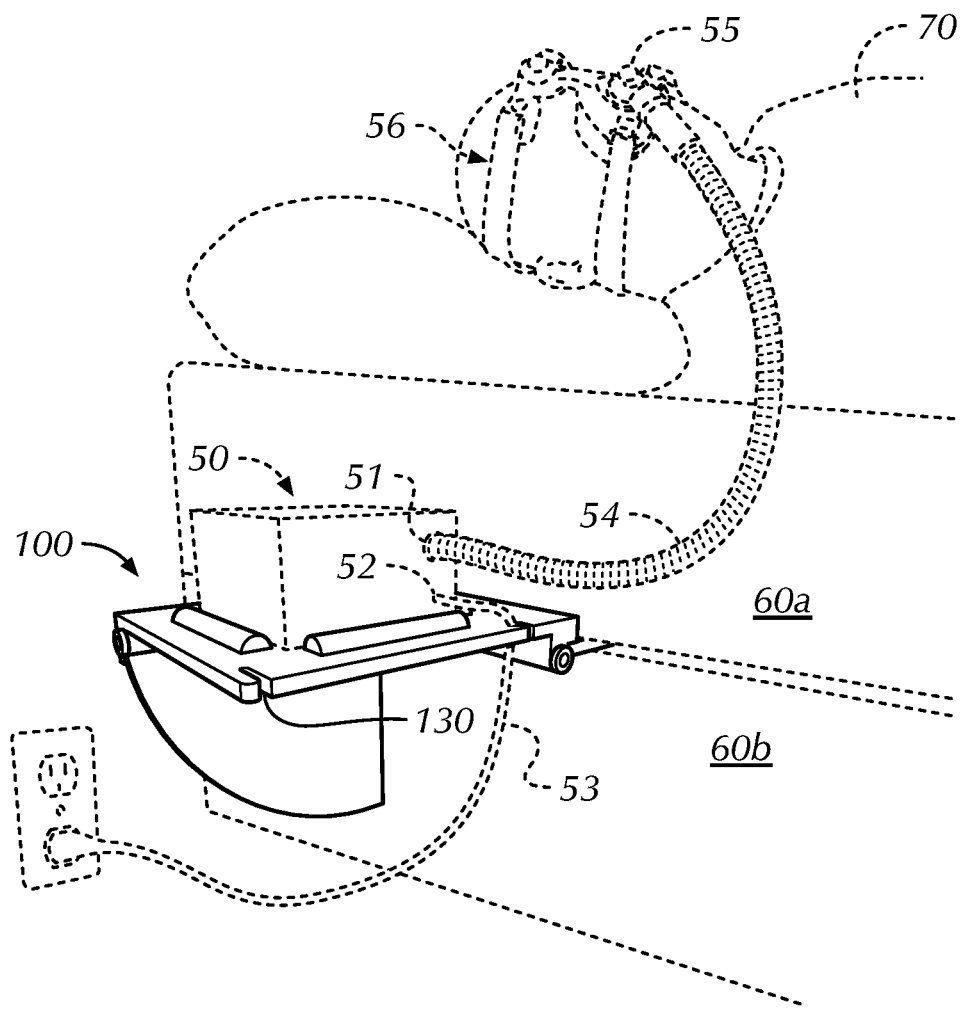
FIG. 1A illustrates a folding table supporting a CPAP machine on the side of a bed during night use by a patient in accordance with an exemplary embodiment of the invention.

Described herein is a folding table for supporting medical equipment bedside. The table comprises three main components which may be folded from an extended position for transport or storage. The folded position is configured to allow the table to be easily transported along with the medical equipment during travel. The table is also configured to be unfolded and stabilized bedside to support the medical equipment without the need of tools, or excessive time or mechanical skills.

The table comprises three main components, the principal being a table top, which supports the medical equipment and has several features to facilitate ease of use for the medical equipment. The secondary components are a support which extends outward from the side of the table at approximately one-hundred eighty degrees (180°), and a stabilizer which extends outward from the bottom of the table so as to be oriented perpendicular to the bottom plane of the table surface, and oriented perpendicular to the common side of the table and support previously described.

The table is designed such that the support is positioned between an upper and lower mattress such that the table top extends beside the bed at approximately the height of the mattresses intersection and parallel with the lying surface of the bed. The stabilizer supports the table top and redirects the downward forces of the table top and its contents approximately ninety degrees (90°) to the side of the lower mattress thus allowing the table top to support heavier loads.

In the preferred embodiment, the table is a molded plastic with a plurality of hinge barrels oriented proximately along the bottom edges of two perpendicular sides of the table. The hinge barrels are offset unequal distances from the bottom of the table surface such that the stabilizer and support, when mated with the table top may be folded against the table's underside to a stacked configuration without interference between the support and stabilizer. One skilled in the art would appreciate that other types of hinges and other configurations of the main components may be utilized within the spirit of the innovation. Examples include, but are not limited to offset hinges, double hinge configurations, removable and attachable stabilizer and/or support. Further, the innovation may be implemented in a non-folding configuration, which would be bulkier for transport, but may be suitable for home, or treatment facility where more consistent use is expected without extensive transportability.

The preferred implementation utilizes a series of machine supports to keep the machine situated on the table during minor bumps, knocks, or other table/bed movements. Alternatives may include utilizing straps, or belts to secure the machine to the table top, sticky pads, suction cups, etc. For some machines, it may be desirable to place a cushioned pad on the table surface to reduce the transmission of vibrations from the machine.

To further protect the machine, from being knocked from the table top, the preferred embodiment comprises a power cord trap. The power cord trap is implemented as an angled groove in one side surface of the table into which a user may guide the power cord such that it is semi-locked or trapped into the groove against casual removal. This power cord trap causes any minor forces on the cord to be transferred to the table top, instead of directly to the machine, or power outlet into which it is connected. Further, if the machine is ever knocked from the table surface, the power cord acts as a restraint to aid in securing the machine to the table, and at least prevent an unrestricted impact with the floor.

The preferred embodiment also includes a mask support hook in the form of a void in one corner of the table which produces a pin, hook, or holder over which a straps of a mask can be hung to support the mask when not in use. Hanging the mask from the strap allows air to pass around the mask during the day to dry any moisture which accumulates during use. This mask hanger, also support the mask in a position conveniently reached for storage and retrieval of the mask by the user. The mask hanger also secures the mask to prevent it from being knocked to the floor, or from taking up space on a bedside table, or the bed lying surface.

The support is a substantially flat planer like surface which can be positioned between the mattresses of a bed without disturbing the lying surface of the bed. In the preferred embodiment the support has a roughened texture to prevent unrestricted slipping from between the mattresses once placed there between. I.E. sufficient force must be applied to remove the support from between the mattresses, and that force amount is dependent on the size of the physical characteristics of the embodiment and the anticipated loads to be placed on the table surface.

The roughened texture should not be sufficiently rough to cause damage to the mattress surfaces, and may include a nonskid material rather than a surface texture. This may be a random texture, or a patterned texture molded, cut, or otherwise embossed or embedded to one or more surfaces of the support. One skilled in the arts would appreciate that dependent on the material construction of the support, the unrestricted slipping from between the mattress may be accomplished by texture, material content, and/or coatings and treatments thereto. The primary requirements would be sufficient resistance from slippage as previously described, and no intentional damage or residue evidence on mattress surfaces after use.

In keeping with the goals of no intentional damage, all surface joints should be deburred, "knocked down," or rounded. Further, the same treatment should apply to all edges which may be exposed to contact during normal expected use. For the same reasoning, the stabilizer in the preferred embodiment having a hinged joint with the bottom surface of the table in the preferred embodiment has a rounded outer edge joining the table contacting edge to avoid having an unnecessary corner protruding from under the table top surface by creating a quarter rounded shape. Other embodiments may have an angled joint producing a triangular shape. In other embodiment, a decorative shape may be utilized, or a plurality of hooks or handles may be molded, cut, or embossed onto one or more surfaces of the stabilizer for hooking or holding hoses, wires, medical devices, etc.

To store or transport the table, the power cord for the machine is removed from the power cord trap, and the machine and mask are removed from the table. The table is then removed from between the mattresses. The stabilizer is folded approximately ninety degrees (90°) to lie flat against the bottom of the table. The support is then folded approximately one hundred eighty degrees (180°) against the bottom of the table, or more specifically against the stabilizer which is against the bottom of the table. One skilled in the arts would appreciate that the exact folding configuration of the table could be altered and still be consistent with the illustrative principals for the innovation described herein. In the folded configuration, the table is approximately the same size as the footprint of the machine, and is substantially flat, and can be easily transported along with the machine.

DETAILED DESCRIPTION OF THE DRAWINGS

FIG. 1A illustrates a folding table supporting a CPAP machine on the side of a bed during night use by a patient in accordance with an exemplary embodiment of the invention. The user (70) lies upon the surface of a bed (60) comprised of an upper mattress (60A) and a lower mattress (60B). A CPAP mask (55), positioned over the face of the user, and held in position with straps (56) connects by air hose (54) to the air intake (51) of a CPAP machine (50).

The machine (50) rest on a table (100) which is positioned beside the bed (60), with the support (300) between the mattresses (60A, 60B) such that the main body of the table (100) protrudes from between the mattresses (60A, 60B) with the table top's stabilizer (200) is against the side of the lower mattress (60B). The power cord (53) is connected to the machine (50) and connected to the power cord trap (140).

The mask support hook, or mask hanger (130) is shown as a notch in one edge of the table (100) distal the support (300) such that the mask (55) will hang away from the bed (60) to promote air circulation around the mask (55) when not in use and supported by the hanger (130).

Figure 1B:
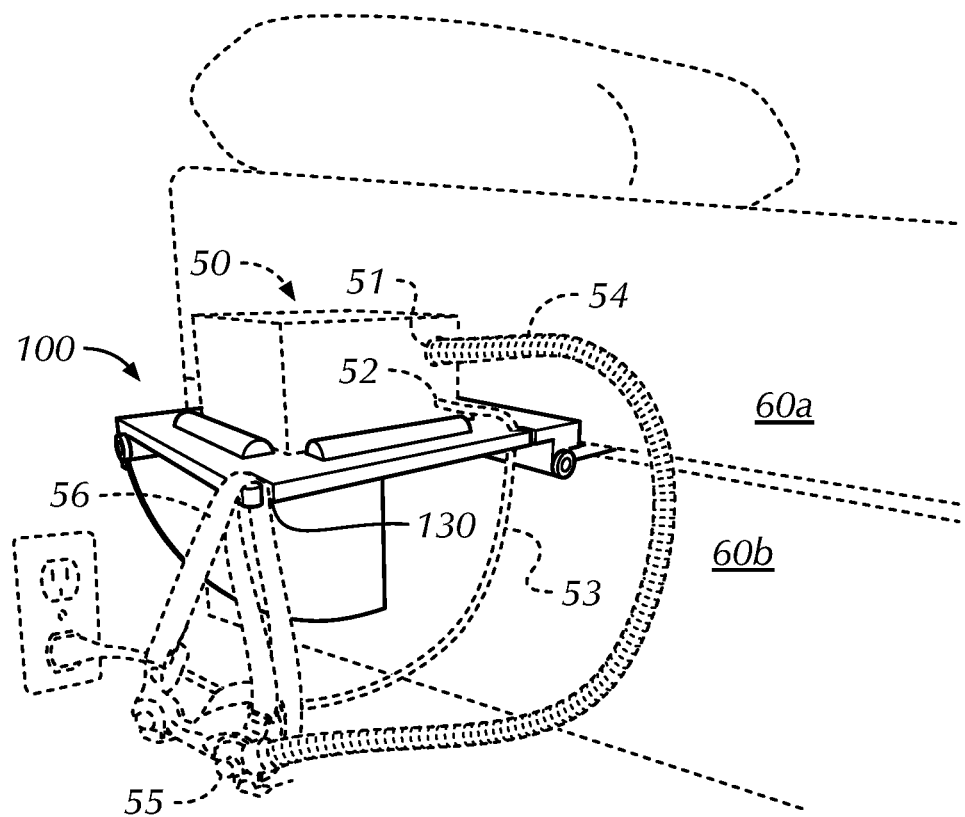
FIG. 1B illustrates a folding table supporting a CPAP machine on the side of a bed during day use with the mask supported by the mask support hook in accordance with an exemplary embodiment of the invention.

FIG. 1B illustrates a folding table supporting a CPAP machine on the side of a bed during day use with the mask supported by the mask support hook in accordance with an exemplary embodiment of the invention. A CPAP mask (55), hangs by the straps (56) from a mask hanger (130) on the edge of the table (100) distal the support (300). The mask (55) connects by air hose (54) to the air intake (51) of a CPAP machine (50). The mask support hook, or mask hanger (130) supports the mask (55) away from the bed (60) to promote air circulation around the mask when not in use.

Figure 2A:
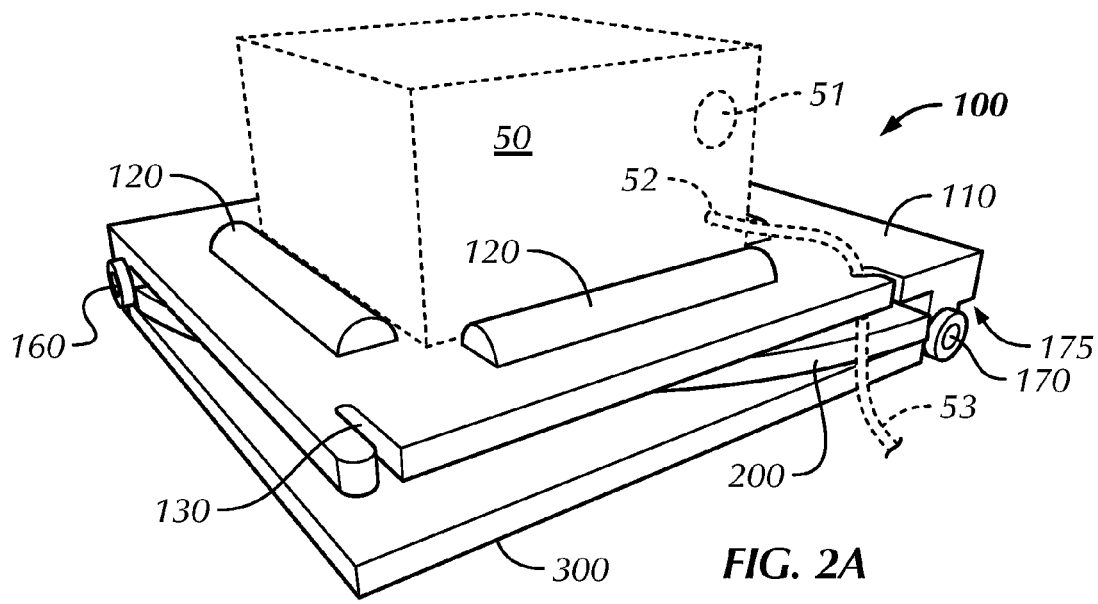
FIG. 2A illustrates a folding table for supporting medical equipment in a folded configuration in accordance with an exemplary embodiment of the invention.
Figure 2B:
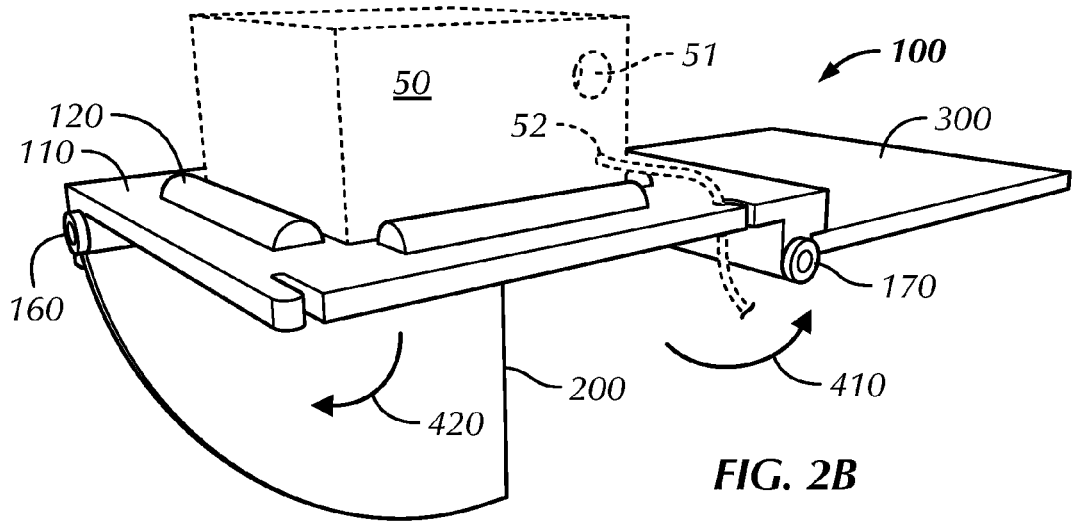
FIG. 2B illustrates a folding table for supporting medical equipment in an extended configuration in accordance with an exemplary embodiment of the invention.

FIG. 2A illustrates a folding table for supporting medical equipment in a folded configuration in accordance with an exemplary embodiment of the invention. FIG. 2B illustrates a folding table for supporting medical equipment in an extended configuration in accordance with an exemplary embodiment of the invention.

The table (100) is sized such that a CPAP machine (50) or other medical device, fits comfortably on the table top (110) and is secured around the edges by machine supports (120). In another embodiment, the machine supports (120) may be closer to the edge of the table top (110), or they may be shaped to accommodate machines (50) which are different shapes. Additionally, the machine supports may be pegs, or pins which insert into one or more receptacles in the table top (110) to allow repositioning such that a universal table top (110) can be customized to hold multiple types of machines (50).

The table top further comprises a mask hanger (130) in an edge, and a power cord trap (140) which in the preferred embodiment illustrated here are created by notches in the edge of the table top (110) and passing completely through the table surface. The table's support (300) is hinged to one side of the table top (110) by hinge joints (170), which allow the support (300) to swing (410) to a position (300') extending away from the table top (110) and substantially parallel. In the preferred embodiment, the support (300, 300') is supported in the extended position by a support hinge stop (175).

The table also includes a stabilizer (200, 200') shown in FIG. 2A in the closed position (200) and in FIG. 2B in the open position (200') having been rotated (420) about a hinge joint (160) to an orientation approximately perpendicular to the table top (110) and perpendicular to the hinge joint (170) of the support (300). The support (300) and the stabilizer (200) may be locked in place by offset hinges, or other locking means which would be familiar to one skilled in the arts. However, in the preferred embodiment illustrated, locking is accomplished by positioning of the support (300) between the mattresses of the bed such that the stabilizer (200) rest against the edge of a bottom mattress (see FIG. 1), preventing the table from closing.

Figure 3A:
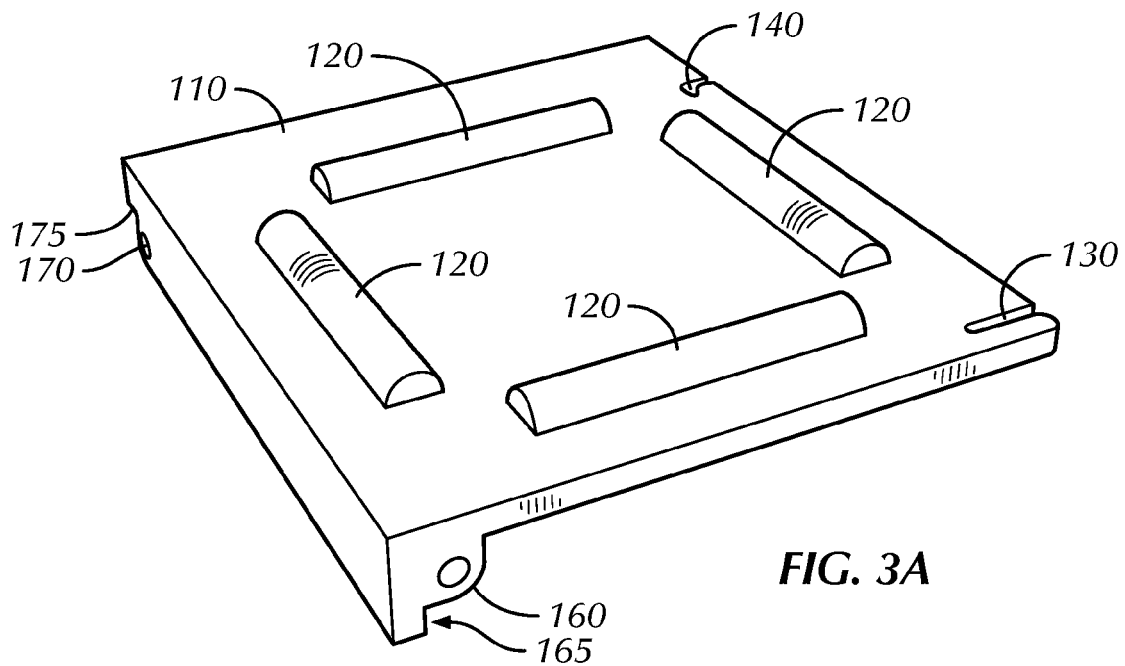
FIG. 3A shows a perspective view from above of the table top component of a folding table in accordance with an exemplary embodiment of the invention.

FIG. 3A shows a perspective view from above of the table top component of a folding table in accordance with an exemplary embodiment of the invention. The table top (110) has machine supports (120) which extend above the table top's (110) top surface. The table top has openings or grooves which pass from the tables top surface to the bottom surface to create notches in the table top.

One such notch creates a mask hanger (130), and is a substantially straight notch located in a corner of the table surface and extending in approximately one half to one inch, being located from the corner approximately a distance equal to the table thickness. The actual dimensions are not specific and are dependent on implementation of the embodiment, being depended on the type of mask to be utilized with the table, and the thickness and strength of the table materials.

Another such notch creates a power cord trap (140), and is a substantially "J" shaped notch located somewhere along a edge of the table surface and extending approximately two times the width of a typical power cord, and then angling approximately ninety degrees. The actual dimensions and shape of the notch are not specific and are dependent on implementation of the embodiment, being depended on the type of power cord to be utilized, and the thickness and strength of the table materials.

Multiple mask hangers (130) and power cord traps (140) can be positioned on the table (100) to allow options for the user to orient the machine (50, not shown) to suit their convenience. In other embodiments, the power cord trap (140) and/or the mask hanger (130) can be extended from the table surface to the side, or above or below the upper or bottom surface, however doing so may compromise the folding and transportability of the table design.

Figure 3B:
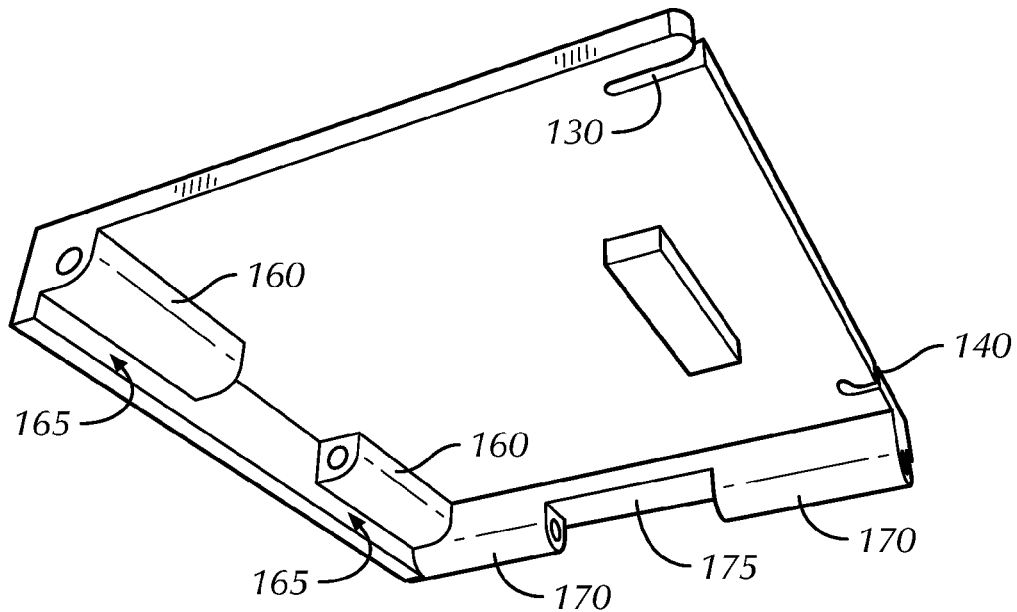
FIG. 3B shows a perspective view from below of the table top component of a folding table in accordance with an exemplary embodiment of the invention.

FIG. 3B shows a perspective view from below of the table top component of a folding table in accordance with an exemplary embodiment of the invention. The table top (110), viewed from the underside shows the mask hanger (130) and the power cord trap (140) since they extend through the table from the upper to the lower surface. Also visible at this angle is a plurality of barrel hinges (160) for the stabilizer (200, not shown) having a hinge support stop (165) which would constrain the hinge to a ninety degree (90°) range between the hinge support stop (165) and the table top's (110) lower surface. Also visible at this angle is a plurality of barrel hinges (170) for the support (300, not shown) having a hinge support stop (175) which would constrain the hinge to a one-hundred eighty degree (180°) range between the hinge support stop (175) and the table top's (110) lower surface.

Figure 4:
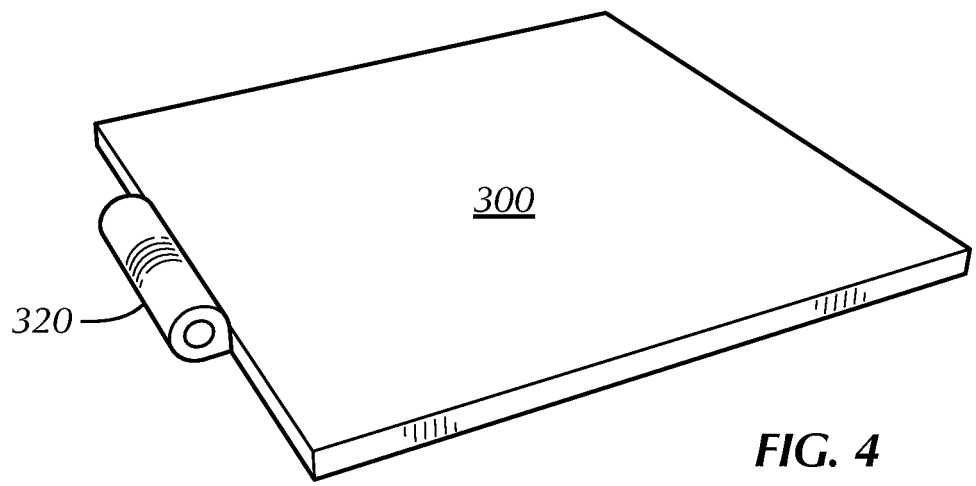
FIG. 4 shows a perspective view from above of the support component of a folding table in accordance with an exemplary embodiment of the invention.

FIG. 4 shows a perspective view from above of the support component of a folding table in accordance with an exemplary embodiment of the invention. The support (300) comprises a barrel hinge (320) located on one edge, which mates with the barrel hinges (170, not shown) of the table top (110, not shown).

Figure 5:
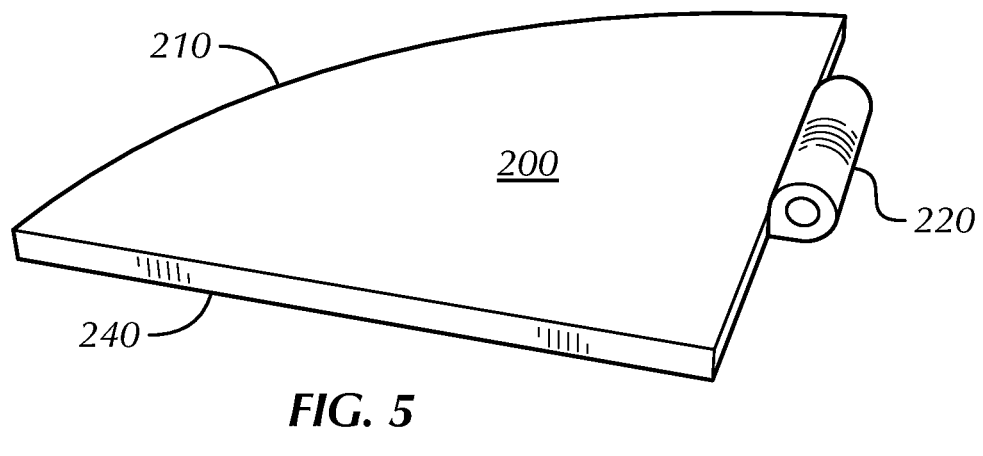
FIG. 5 shows a perspective view from above of the stabilizer component of a folding table in accordance with an exemplary embodiment of the invention.

FIG. 5 shows a perspective view from above of the stabilizer component of a folding table in accordance with an exemplary embodiment of the invention. The stabilizer (200) comprises a barrel hinge (220) located on one edge, which mates with the barrel hinges (160, not shown) of the table top (110, not shown). The table has a supporting edge (240) which is a straight edge perpendicular to the axis of the barrel hinges (220). In the preferred embodiment, a curved edge (210) joints the supporting edge (240) and the perpendicular edge containing the barrel hinges (220) to create an approximate quarter round shape. This configuration means no corners protrude from under the table surface which may cause a hazard.

Figure 6:
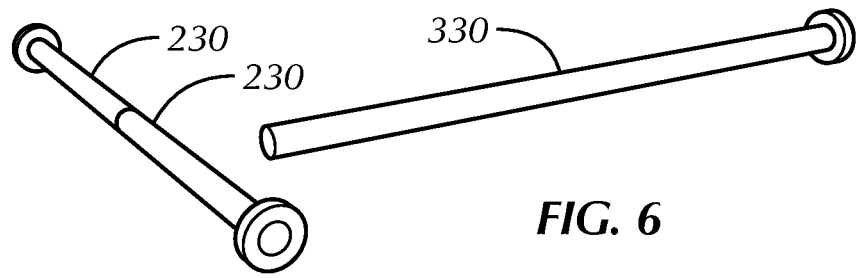
FIG. 6 shows a perspective view of hinge pins for a folding table in accordance with an exemplary embodiment of the invention.

FIG. 6 shows a perspective view of hinge pins for a folding table in accordance with an exemplary embodiment of the invention. In the preferred embodiment barrel hinges (220 and 160) were utilized for joining the support to the table top and barrel hinges (320 and 170) were utilized for joining the stabilizer to the table top. In the preferred embodiment, a plurality of hinge pins (230) extend from either end of the support to meet in the middle of the center barrel (220) of the three barrel configuration. Due to the positioning of the stabilizer in the preferred embodiment, a single hinge pin (330) was utilized for the three barrel configuration of the support. One skilled in the arts would appreciate many other configurations and hinge joints, types, and orientations that may accomplish the same general functions and would be in accordance with the illustrative principals of the innovation described herein.

The diagrams in accordance with exemplary embodiments of the present invention are provided as examples and should not be construed to limit other embodiments within the scope of the invention. For instance, heights, widths, and thicknesses may not be to scale and should not be construed to limit the invention to the particular proportions illustrated. Additionally some elements illustrated in the singularity may actually be implemented in a plurality. Further, some element illustrated in the plurality could actually vary in count. Further, some elements illustrated in one form could actually vary in detail. Further yet, specific numerical data values (such as specific quantities, numbers, categories, etc.) or other specific information should be interpreted as illustrative for discussing exemplary embodiments. Such specific information is not provided to limit the invention.

The above discussion is meant to be illustrative of the principles and various embodiments of the present invention. Numerous variations and modifications will become apparent to those skilled in the art once the above disclosure is fully appreciated. It is intended that the following claims be interpreted to embrace all such variations and modifications.

What is claimed is:
1. A bedside table comprising;
    a table top;
    a support extending from one edge of the table top,
        wherein the support is configured for positioning between an upper and a lower bed component; and
        is supported by the bed components without permanent mounting thereto wherein the table does not require reconfiguration due to varying distance from the position to the floor, is independent of such distance; and wherein the table may be moved horizontally between the upper and lower bed component to be variably positioned between the head and foot of the bed;

a stabilizer extending down from a bottom surface of the table top and contained wholly beneath the table top, wherein at least one surface of the stabilizer is configured to prevent the table top from sliding between the upper and lower bed component, and the stabilizer is positioned to direct the weight of the table and any containing objects toward the side of the lower bed component;

wherein the table is configured to support a constant positive airway pressure machine wherein the configuration comprises:

an accessory support to secure the facial mask of the constant positive airway pressure machine in the air away from potentially contaminating surfaces, the support extending through the table top surface to the bottom surface, and extending into the table at a perpendicular angle to the edge of the table from a point near a corner of the table.

2. A bedside table as described in claim 1 wherein the support is rotationally connected to the table top such that the support rotates in a downward arc to alternate between a folded position substantially aligned with the table top, and adjacent to the underside of the table, and an extended position extending from one side of the table top and substantially parallel to the tabletop; and the stabilizer is rotationally connected to the table top such that the stabilizer rotates in an arc to alternate between a folded position substantially aligned with the table top, and adjacent to the underside of the table, and an extended position extending downward from the table top and substantially perpendicular to the tabletop such that the table can be configured into an extended position for usage as a bedside table, or folded to a substantially flat configuration for transport with the constant positive airway pressure machine.

3. A bedside table as described in claim 1 further comprising:

a power cord trap for securing the constant positive airway pressure machine to the table;

the power cord trap comprising:

a notch extended from the top surface through the table top to the bottom surface extending into the table from an edge and angling to at least one side.

* * * * *